(12) United States Patent
Ivachtchenko

(10) Patent No.: US 10,450,278 B2
(45) Date of Patent: Oct. 22, 2019

(54) SUBSTITUTED 2-THIOXO-IMIDAZOLIDIN-4-ONES AND SPIRO ANALOGUES THEREOF, ACTIVE ANTICANCER INGREDIENT, PHARMACEUTICAL COMPOSITION, MEDICINAL PREPARATION, METHOD FOR TREATING PROSTATE CANCER

(71) Applicant: R-Pharm Overseas Inc., Wilmington, DE (US)

(72) Inventor: Alexandre Vasilievich Ivachtchenko, Moskovskaya (RU)

(73) Assignee: R-Pharm Overseas Inc., Wilmington, DE (US)

( * ) Notice: Subject to any disclaimer, the term of this patent is extended or adjusted under 35 U.S.C. 154(b) by 0 days.

(21) Appl. No.: 15/324,658

(22) PCT Filed: Jun. 26, 2015

(86) PCT No.: PCT/RU2015/000395
§ 371 (c)(1),
(2) Date: Jan. 6, 2017

(87) PCT Pub. No.: WO2016/007046
PCT Pub. Date: Jan. 14, 2016

(65) Prior Publication Data
US 2018/0179164 A1 Jun. 28, 2018

(30) Foreign Application Priority Data
Jul. 8, 2014 (RU) .................................. 2014127705

(51) Int. Cl.
| | | |
|---|---|---|
| C07D 233/86 | (2006.01) | |
| C07D 491/107 | (2006.01) | |
| C07D 307/24 | (2006.01) | |
| C07C 229/60 | (2006.01) | |
| C07C 227/16 | (2006.01) | |
| A61P 35/00 | (2006.01) | |
| A61K 31/4166 | (2006.01) | |
| A61K 31/4188 | (2006.01) | |

(52) U.S. Cl.
CPC ........ *C07D 233/86* (2013.01); *A61K 31/4166* (2013.01); *A61K 31/4188* (2013.01); *A61P 35/00* (2018.01); *C07C 227/16* (2013.01); *C07C 229/60* (2013.01); *C07D 307/24* (2013.01); *C07D 491/107* (2013.01); *C07B 2200/07* (2013.01)

(58) Field of Classification Search
CPC . A61K 31/4166; A61K 31/4188; A61P 35/00; C07D 233/86; C07D 491/107; C07D 307/24; C07B 2200/07; C07C 227/16; C07C 229/60
See application file for complete search history.

(56) References Cited

U.S. PATENT DOCUMENTS

| | | | |
|---|---|---|---|
| 9,073,874 B2 * | 7/2015 | Ivachtchenko | ...... C07D 233/72 |
| 2016/0016925 A1 * | 1/2016 | Ivachtchenko | ...... C07F 7/0812 |
| | | | 548/301.4 |

FOREIGN PATENT DOCUMENTS

| | | |
|---|---|---|
| RU | 2434851 C1 | 11/2011 |
| RU | 2520134 C1 | 6/2014 |
| WO | 2006124118 A1 | 11/2006 |
| WO | 2011106570 A1 | 9/2011 |
| WO | 2012011840 A1 | 1/2012 |

OTHER PUBLICATIONS

A. Ivachtchenko et al., 99 European Journal of Medicinal Chemistry, 51-66 (2015).*
Cochrane, Dawn R. et al., "Abstract LB-109: MDV3100, an androgen receptor signaling inhibitor, inhibits tumor growth in breast cancer preclinical models regardless of estrogen receptor status", Proceedings: AACR 103rd Annual Meeting 2012—Mar. 31-Apr. 4, 2012; Chicago, IL; American Association for Cancer Research, vol. 72, Issue 8, Supplement 1, Apr. 2012, 3 pages.
Ivachtchenko, Alexandre V. et al., "Preclinical Development of ONC1-13B, Novel Antiandrogen for Prostate Cancer Treatment", Journal of Cancer, vol. 5, No. 2, Jan. 21, 2014, pp. 133-142.
Rathkopf, Dana E. et al., "Phase I Study of ARN-509, a Novel Antiandrogen, in the Treatment of Castration-Resistant Prostate Cancer", Journal of Clinical Oncology, vol. 31, No. 28, Oct. 1, 2013, pp. 3525-3531.

(Continued)

*Primary Examiner* — Alexander R Pagano
*Assistant Examiner* — Ebenezer O Sackey
(74) *Attorney, Agent, or Firm* — Kolisch Hartwell, P.C.

(57) ABSTRACT

Novel (R)-stereoisomers of substituted 2-thioxo-imidazolidin-4-ones of formula 1, or spiro analogues thereof, which exhibit androgen receptor antagonist properties. Also provided are variants of a method for producing the same, intermediate compounds for producing compounds of formula 1, and pharmaceutical compositions containing compounds of formula 1 in the form of tablets, capsules, and/or injections. Compounds of formula 1 can be used to produce a medicinal agent suitable for treating cancers, such as prostate cancer and breast cancer. The compounds of formula 1 may have the structure:

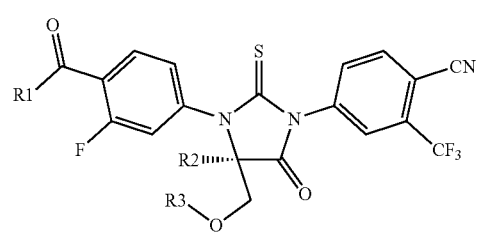

wherein R1 is OH, NH$_2$, or an OR4 group;
R2 and R3 are methyl, or
R2 and R3 are a CH$_2$—CH$_2$ group; and
R4 is C$_1$-C$_4$ alkyl or cyclopropyl.

19 Claims, No Drawings

(56) References Cited

OTHER PUBLICATIONS

Sanford, Mark, "Enzalutamide: A Review of Its Use in Metastatic, Castration-Resistant Prostate Cancer", Adis Drug Evaluation, vol. 73, Oct. 15, 2013, pp. 1723-1732.
Russian Patent Office, "International Search Report" in connection with related International Patent Application No. PCT/RU2015/000395, dated Nov. 26, 2015, 2 pages.

\* cited by examiner

SUBSTITUTED 2-THIOXO-IMIDAZOLIDIN-4-ONES AND SPIRO ANALOGUES THEREOF, ACTIVE ANTICANCER INGREDIENT, PHARMACEUTICAL COMPOSITION, MEDICINAL PREPARATION, METHOD FOR TREATING PROSTATE CANCER

TECHNICAL FIELD

The invention relates to novel (R)-stereoisomers of substituted 2-thioxo-imidazolidin-4-ones and spiro analogues thereof, active anticancer ingredient, pharmaceutical composition, anticancer medicinal preparation, method for treating prostate cancer and breast cancer.

PRIOR ART

There are known antagonists of the androgen receptors comprising substituted 2-thioxo-imidazolidin-4-ones I [(a) WO/2006/124118 A1; (b) Sanford, M. Enzalutamide: A Review of Its Use in Metastatic, Castration-Resistant Prostate Cancer. *Drugs* (2013), 73(15), 1723-1732, DOI: 10.1007/s40265-013-0129-9] and II WO/2012/011840].

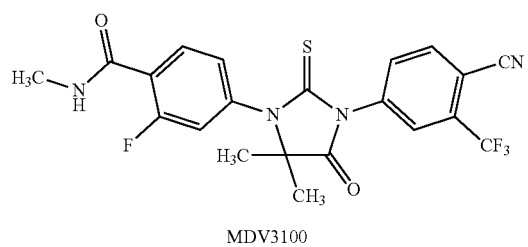

MDV3100

$IC_{50} = 124.7$ nM
$K_i = 28.6$ nM

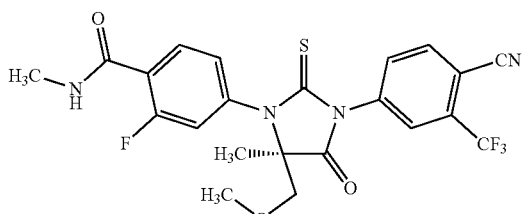

H030-0016B $IC_{50} = 145.3$ nM
$K_i = 34.9$ nM

There are also known antagonists of the androgen receptors comprising substituted spiro analogues of 2-thioxo-imidazolidin-4-ones III [Rathkopf D E¹, Morris M J, Fox J J, Danila D C, Slovin S F, Hager J H, Rix P J, Chow Maneval E, Chen I, Gönen M, Fleisher M, Larson S M, Sawyers C L, Scher H I. Phase I study of ARN-509, a novel antiandrogen, in the treatment of castration-resistant prostate cancer. *J Clin Oncol.* 2013 Oct. 1; 31(28):3525-30. doi: 10.1200/JCO.2013.50.1684. Epub 2013 Sep. 3.] and IV [(a) WO/2012/011840; (b) Ivachtchenko, A. V.; Mitkin, O. D.; Kudan, E. V.; Rjahovsky, A. A.; Vorobiev, A. A.; Trifelenkov, A. S.; Shevkun, N. A.; Proskurina, O. V.; Kravchenko, D. V.; Karapetian, R. N. Preclinical Development of ONC1-13B, Novel Antiandrogen for Prostate Cancer Treatment. *J. Cancer* 2014; 5(2): 133-142. doi: 10.7150/jca.7773.]

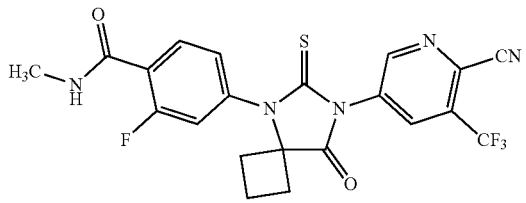

ARN-509

$IC_{50} = 171.9$ nM
$K_i = 33.3$ nM

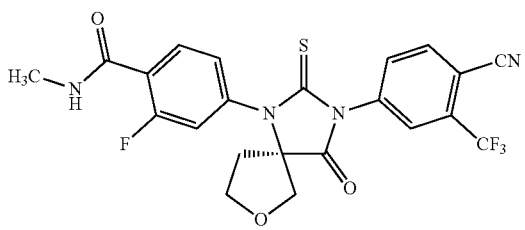

ONC1-0013B $IC_{50} = 83.5$ nM
$K_i = 20.1$ nM

Antagonists of the androgen receptors III and IV are currently at the stage of clinical trials, and antagonist I, known as Enzalutamide and Xtandi, formerly known as MDV3100, was approved by FDA in August 2012 for the treatment of prostate cancer [http://en.wikipedia.org/wiki/Enzalutamide].

It is also known that antagonists of the androgen receptors provide new perspectives for breast cancer treatment [D. R. Cochrane, B. M. Jacobsen, D. M. Cittelly, E. N. Howe, A. Jean, N. S. Spoelstra, S. Bernales, A. A. Protter, A. D. Elias, J. K. Richer. Abstract LB-109: MDV3100, an androgen receptor signaling inhibitor, inhibits tumor growth in breast cancer preclinical models regardless of estrogen receptor status. *Cancer Research*: Apr. 15, 2012; Volume 72, Issue 8, Supplement 1. doi: 10.1158/1538-7445.AM2012-LB-109. Proceedings: AACR 103rd Annual Meeting Mar. 31-Apr. 4, 2012; Chicago, Ill. 2012 American Association for Cancer Research. http://cancerres.aacrjournals.org/cgi/content/short/72/8_MeetingAbstracts/LB-109?rss=1].

In view of the positive results of clinical trials of androgen receptor antagonists for prostate cancer treatment, a search for more effective anticancer medicinal products with increased potency and reduced toxicity remains one of the main activities to develop new pharmacological agents for cancer treatment, including treatment of prostate cancer. Therefore, it is essential to develop new anticancer agents, pharmaceutical compositions, and medicinal products, as well as methods for production and use thereof.

DISCLOSURE OF INVENTION

Definitions for the terms used in the invention description are provided below.

"Alkyl" means a linear or branched aliphatic hydrocarbon group with 1-12 carbon atoms in the chain. "Brached"

means that alkyl chain has one or more "lower alkyl" substituents. Alkyl can have one or more identical or different substituents ("alkyl substituents") including halogen, alkenyloxy, cycloalkyl, aryl, heteroaryl, heterocyclyl, aroyl, cyano, hydroxy, alkoxy, carboxy, alkynyloxy, aralkoxy, aryloxy, ariloxycarbonyl, alkylthio, heteroarylthio, aralkylthio, arylsulfonyl, alkylsulfonylheteroaralkyloxy, etc.

"Alkyloxy", or "Alkoxy" means an alkyl-O— group, wherein alkyl is as defined in this section. Preferred alkyoxy groups are methoxy, ethoxy, n-propoxy, iso-propoxy and n-butoxy.

"Aryl" means an aromatic monocyclic or polycyclic system comprising from 6 to 14 carbon atoms, chiefly from 6 to 10 carbon atoms. Aryl can have one or more ring system substituents, which can be identical or different. Examples of aryl groups: phenyl or naphthyl, substituted phenyl or substituted naphthyl. Aryl can be annulated to nonaromatic cyclic system or heterocycle.

"Heterocycle" means an aromatic or nonaromatic saturated mono- or polycyclic system comprising from 3 to 10 carbon atoms, chiefly from 5 to 6 carbon atoms, wherein one or more carbon atoms are substituted by a heteroatom, such as nitrogen, oxygen, sulfur. Prefix aza-, oxa- or thia- before a heterocycle means the presence in a cyclic system of a hydrogen atom, oxygen atom or sulphur atom respectively. A heterocycle can have one or more cyclic system substituents, which can be identical or different. Heterocyclic atoms of nitrogen and sulphur can be oxidized to N-oxide, S-oxide or to S-dioxide. Examples of heterocycles: piperidine, pyrrolidine, piperazine, morpholine, thiomorpholine, thiazolidinedione, 1,4-dioxane, tetrahydrofuran, tetrahydrothiophene, etc.

"Hydrate" means a compound formed by the addition of water (hydration) to molecules, atoms or ions.

"Substituent" means a chemical radical attached to a scaffold (fragment), for example, "alkyl substituent", "substituent of the amine group", "carbamoyl substituent", "substituent of a cyclic system", as defined in this section.

"Drug substance" means a physiologically active ingredient of synthetic or another (biotechnological, herbal, animal, microbial, etc.) origin which is pharmacologically active and is an active agent of a pharmaceutical composition intended for production and formulation of medicinal products (drugs).

"Medicinal product (drug)" is a substance (or combination of substances in the form of pharmaceutical composition) in tablets, capsules, injections, ointments and other finished dosage forms intended for restoration, cure or change of physiological functions in humans and animals, as well as treatment and prevention of diseases, diagnosis, anesthesia, interception, cosmetology, etc.

"Lower alkyl" means a linear or branched alkyl with 1-4 carbon atoms.

"Therapeutic cocktail" is simultaneously administered combination of two or more medicinal products with different mechanisms of pharmacological action and targeting different biological targets involved in pathogenesis of a disease.

"Pharmaceutical composition" means a composition comprising a compound of formula 1 and at least one of the components selected from a group consisting of pharmaceutically acceptable and pharmacologically compatible fillers, solvents, diluents, vehicles, auxiliary, distributing and perceiving agents, delivery agents, such as preservatives, stabilizers, fillers, disintegrants, moisturizers, emulsifiers, suspending agents, gelifiers, sweeteners, flavours, antibacterial agents, fungicides, lubricants, extended release agents, the choice and proportion of which depends on the nature and the way of administration and dosage. The examples of suspending agents: ethoxylated isostearyl alcohol, polyoxyethylene, sorbitol and sorbitol ester, microcrystalline cellulose, aluminium hydroxide oxide, bentonite, agar-agar and tragacanth, as well as mixtures of these substances. Protection from the actions of micro-organisms can be achieved through the use of various antibacterial and antifuginal agents, such as, for example, parabens, chlorobutanol, sorbic acid and similar compounds. A composition may include isotonic agents as well, for example, sugars, sodium chloride and similar to them. Sustained action of a composition can be achieved through the agents which delay absorption of an active agent, for example, aluminum monostearate and gelatin. Water, ethanol, polyalcohols, and mixtures thereof, vegetable oils (such as olive oil) and injectable organic esters (such as ethyl oleate) are examples of suitable vehicles, solvents, diluents and delivery agents. The examples of fillers are lactose, sodium citrate, calcium carbonate, calcium phosphate and similar to them. The examples of disintegrants and disintegrants are starch, alginic acid and salts thereof, silicates. The examples of lubricants are magnesium stearate, sodium lauryl sulphate, talc, as well as polyethylene glycol having high molecular weight. A pharmaceutical composition for oral, sublingual, transdermal, intramuscular, intravenous, subcutaneous, topical or rectal administration of an active agent, alone or in combination with another active agent, can be administered to animals and humans in a standard administration form as a mixture with conventional pharmaceutical vehicles. Suitable standard administration forms include those for oral administration, such as tablets, gelatin capsules, pills, powders, granules, chewing gum and oral solution or suspension, for sublingual and transbuccal administration, aerosols, implants, dosage foems for topical, transdermal, subcutaneous, intramuscular, intravenous, intranasal or intraocular and rectal administration. Pharmaceutical compositions are produced, as a rule, through standard procedures, which provide for the mixing of an active compound with a liquid or finely ground solid vehicle.

Known antagonists of the androgen receptors I-IV include 2-fluoro-N-methyl-4-(4-oxo-2-thioxo-imidazolidin-1-yl)-benzamide fragment. We have surprisingly found out that novel antagonists of the androgen receptors which contain 2-fluoro-4-(4-oxo-2-thioxo-imidazolidin-1-yl)-benzamide fragment or a fragment of 2-fluoro-4-(4-oxo-2-thioxo-imidazolidin-1-yl)-benzoic acid or alkyl or cycloalkyl ester thereof instead of the said fragment demonstrate higher antagonistic activity against androgen receptors.

Subject matter of this invention is novel substituted 2-thioxo-imidazolidine-4-ones and their spiro analogues expressed by the general formula 1,

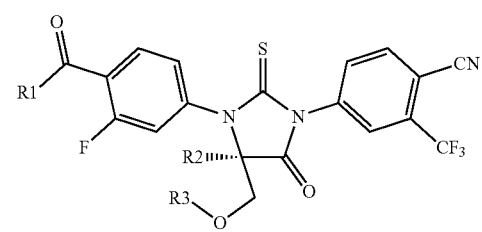

1 wherein
R1 is OH, NH₂, or a OR4 group;
R2 and R3 are methyl, or
R2 and R3 together are a CH₂—CH₂ group;
R4 is C₁-C₄ alkyl or cyclopropyl.

Preferred compounds are substituted 2-thioxo-imidazolidine-4-ones, or their spiro analogues, expressed by the general formula 1.1 and 1.2, 1.1

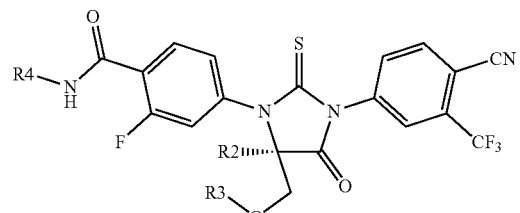

1.2

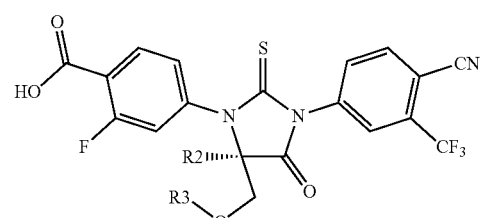

wherein R2, R3, and R4 are as defined above.

More preferred compounds are
methyl 4-[(R)-3-(3-methyl-4-cyano-phenyl)-5-methyl-5-methoxymethyl-4-oxo-2-thioxo-imidazolidin-1-yl]-2-fluoro-benzoate 1.1.1,
methyl 4-[(R)-3-(3-methyl-4-cyano-phenyl)-4-oxo-2-thioxo-7-oxa-1,3-diaza-spiro[4.4]non-1-yl]-2-fluoro-benzoate 1.1.2,
isopropyl 4-[(R)-3-(3-methyl-4-cyano-phenyl)-4-oxo-2-thioxo-7-oxa-1,3-diaza-spiro[4.4]non-1-yl]-2-fluoro-benzoate 1.1.3,
cyclopropyl 4-[(R)-3-(3-methyl-4-cyano-phenyl)-4-oxo-2-thioxo-7-oxa-1,3-diaza-spiro[4.4]non-1-yl]-2-fluoro-benzoate 1.1.4,
4-[(R)-3-(3-methyl-4-cyano-phenyl)-5-methyl-5-methoxymethyl-4-oxo-2-thioxo-imidazolidine-1-yl]-2-fluoro-benzoic acid 1.2.1,
4-[(R)-3-(3-methyl-4-cyano-phenyl)-4-oxo-2-thioxo-7-oxa-1,3-diaza-spiro[4.4]non-1-yl]-2-fluoro-benzoic acid 1.2.2,
4-[(R)-3-(3-methyl-4-cyano-phenyl)-5-methyl-5-methoxymethyl-4-oxo-2-thioxo-imidazolidine-1-yl]-2-fluoro-benzamide 1.3.1, or
4-[(R)-3-(3-methyl-4-cyano-phenyl)-4-oxo-2-thioxo-7-oxa-1,3-diaza-spiro[4.4]non-1-yl]-2-fluoro-benzamide 1.3.2.

1.1.1

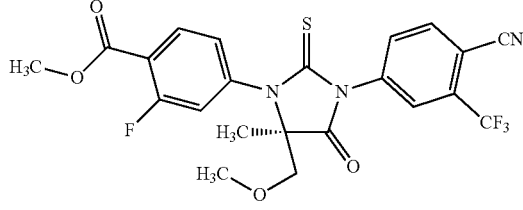

1.1.2

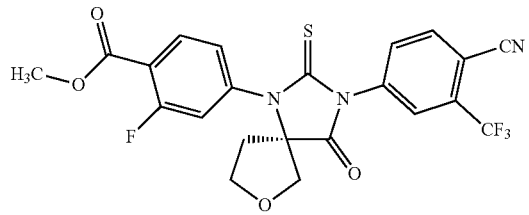

1.1.3

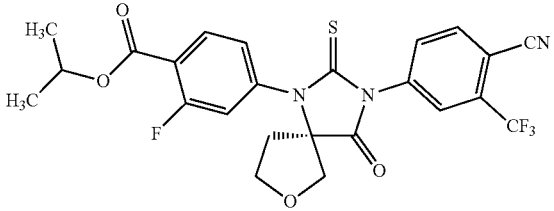

1.1.4

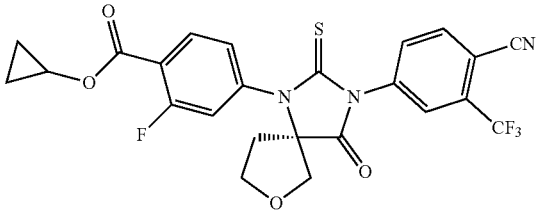

1.2.1

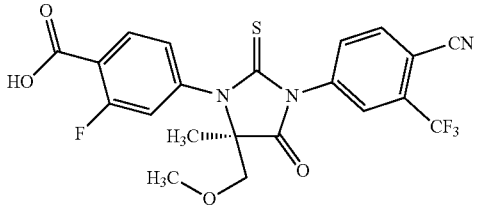

1.2.2

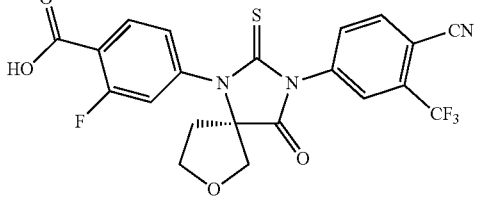

1.3.1

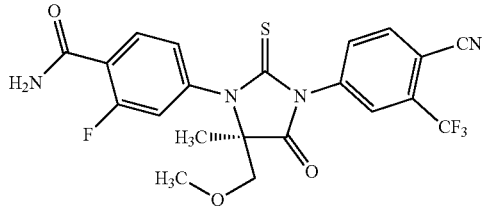

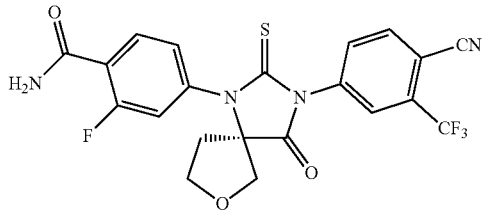
1.3.2

Subject matter of this invention is compounds selected from the group comprising 4-((R)-1-carboxy-1-methyl-2-methoxy-ethylamino)-2-fluoro-benzoic acid 2.1, (R)-3-(4-carboxy-3-fluoro-phenylamino)-tetrahydrofurane-3-carboxylic acid 2.2, methyl 4-((R)-1-methyl-2-methoxy-1-methoxycarbonyl-ethylamino)-2-fluoro-benzoate 2.3, and methyl (R)-3-(4-methoxycarbonyl-3-fluoro-phenylamino)-tetrahydrofurane-3-carboxylate 2.4, which are intermediate products for the synthesis of compounds expressed by the general formula 1.

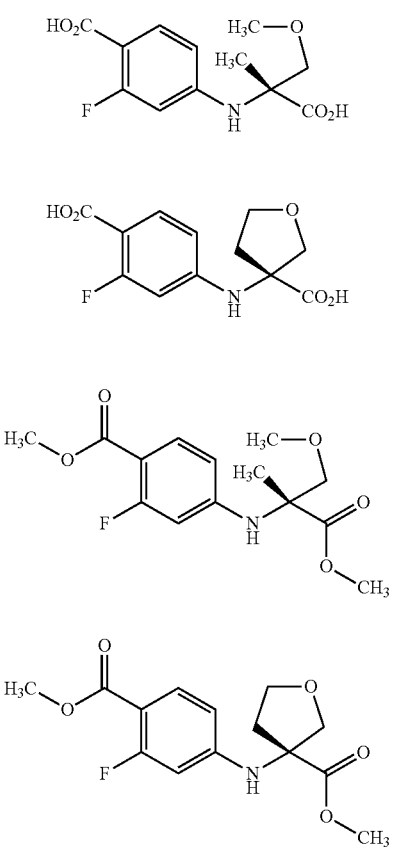

2.1

2.2

2.3

2.4

Subject matter of this invention is a method for the production of compounds expressed by the general formula 2.1 and 2.2, which consists in reaction between (R)-stereoisomer of the amino acid expressed by the general formula 3.1 and 4-bromo-2-fluorobenzoic acid 3.2 in dimethylformamide in the presence of CuI and a base at elevated temperatures (FIG. 1).

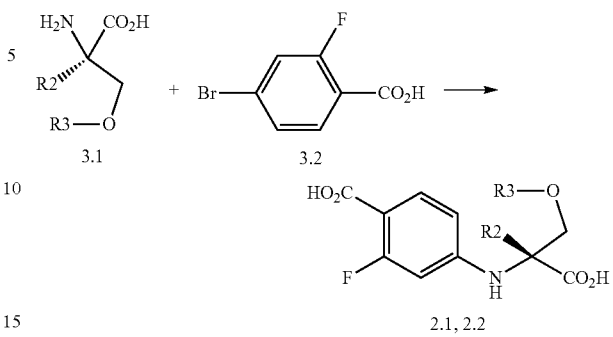

Figure 1.

3.1  3.2

2.1, 2.2 wherein R2═R3═CH$_3$ or R2 together with R3 are a CH$_2$—CH$_2$ group.

Subject matter of this invention is a method for the production of compounds expressed by the general formula 2.3 and 2.4, which consists in reaction between the relevant (R)-stereoisomers of diacids 2.1 and 2.2 and alcohol in the presence of thionyl chloride (FIG. 2).

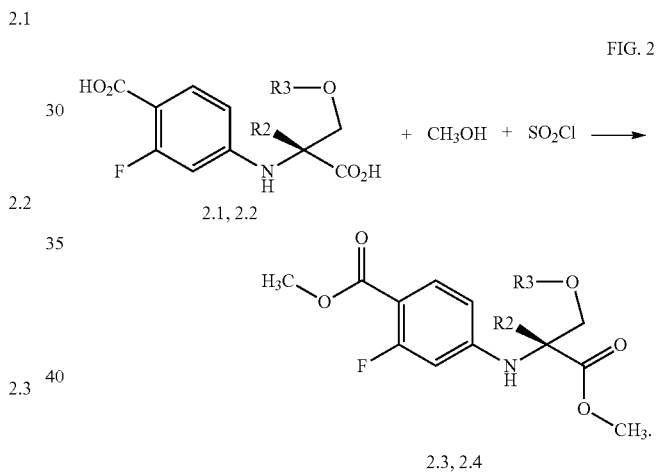

FIG. 2

2.1, 2.2

2.3, 2.4 wherein R2═R3═CH$_3$ or R2 together with R3 are a CH$_2$—CH$_2$ group.

Subject matter of this invention is a method for the production of compounds expressed by the general formula 1.1.1, 1.1.2, which consists in reaction between the relevant (R)-stereoisomers of diesters 2.3 and 2.4 and 4-cyano-3-trifluoromethyl-benzylisothiocyanate 3.3 at elevated temperatures (FIG. 3).

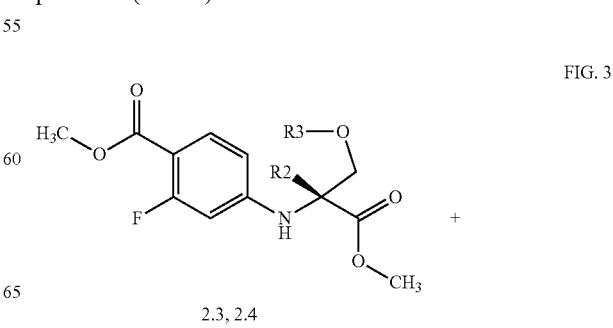

FIG. 3

2.3, 2.4

-continued

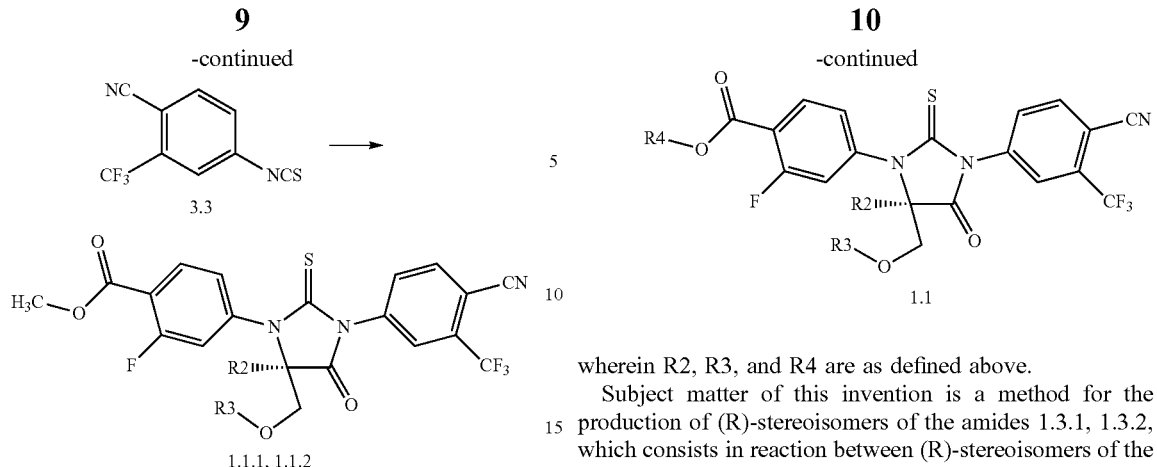

1.1.1, 1.1.2 wherein R2 and R3 are as defined above.

Subject matter of this invention is a method for the production of (R)-stereoisomers of the acids expressed by the formula 1.2.1, 1.2.2 through alkaline hydrolysis of (R)-stereoisomers of esters expressed by the general formula 1.1.1, 1.1.2 (FIG. 4).

FIG. 4

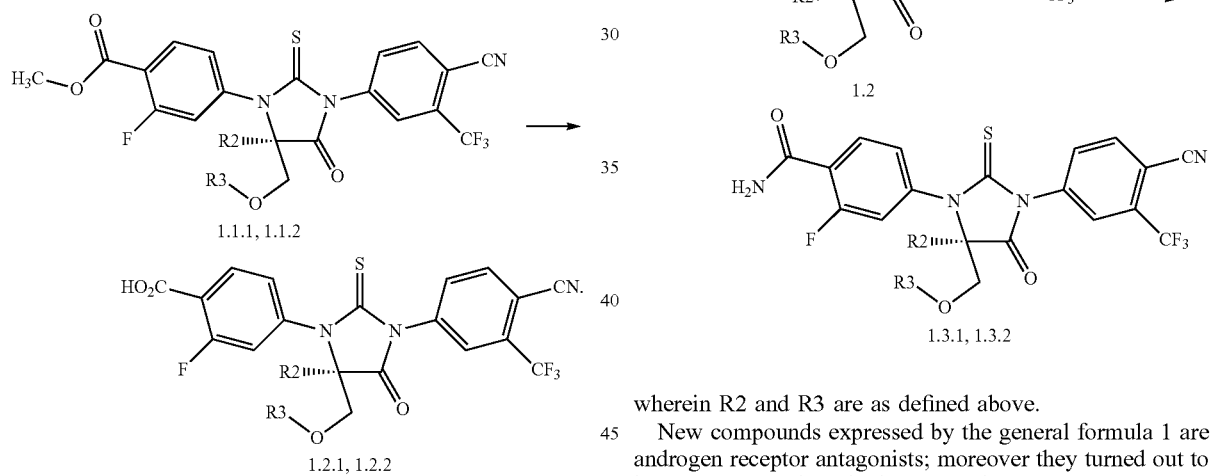

1.1.1, 1.1.2

1.2.1, 1.2.2 wherein R2 and R3 are as defined above.

Subject matter of this invention is a method for the production of (R)-stereoisomers of the esters expressed by the general formula 1.1, which consists in reaction between (R)-stereoisomers of the acids expressed by the formula 1.2 and R$_4$OH alcohol and thionyl chloride (FIG. 5).

Figure 5.

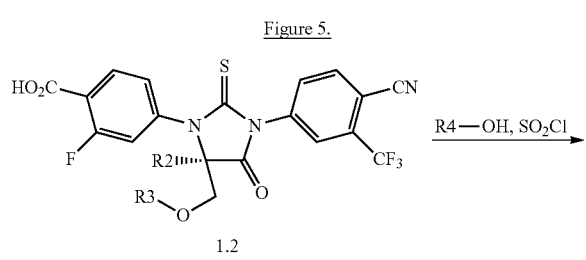

1.2

-continued

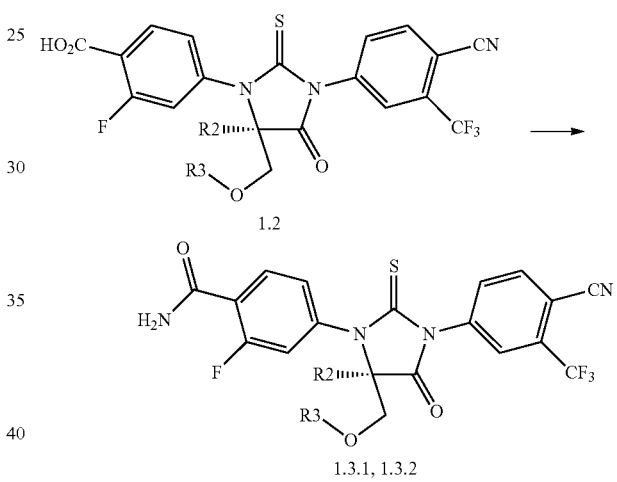

1.1 wherein R2, R3, and R4 are as defined above.

Subject matter of this invention is a method for the production of (R)-stereoisomers of the amides 1.3.1, 1.3.2, which consists in reaction between (R)-stereoisomers of the acids expressed by the general formula 1.2 and ammonium chloride in the presence of N-(3-dimethylaminopropyl)-N'-ethylcarbodiimide, 1-hydroxybenzotriazole, and triethylamine in dimethylformamide (FIG. 6).

FIG. 6

1.2

1.3.1, 1.3.2 wherein R2 and R3 are as defined above.

New compounds expressed by the general formula 1 are androgen receptor antagonists; moreover they turned out to be more potent than the known androgen receptor antagonists (Table 1). As shown in the Table 1, new compounds are more potent than the known analogues thereof, the most potent is compound 1.1.2 with $K_i$=5.6 nM, which is 5.1 times more potent than MDV3100, 5.9 times more potent than ARN-509, and 3.6 times more potent than ONC1-0013B. It should be noted that higher potency of the drugs enables the use of lower doses in treatment of cancer, which, all other things being equal, reduces the toxicity, and therefore reduces side effects.

Subject matter of this invention is a novel anticancer active ingredient comprising at least one compound expressed by the general formula 1.

Subject matter of this invention is also a pharmaceutical composition which possesses anticancer activity and contains at least one compound expressed by the general formula 1 as an active ingredient.

More preferred is a pharmaceutical composition intended for treatment of prostate cancer which contains at least one compound expressed by the general formula 1 as an active ingredient.

More preferred is also a pharmaceutical composition intended for treatment of breast cancer which contains at least one compound expressed by the general formula 1 as an active ingredient.

The pharmaceutical compositions may include pharmaceutically acceptable excipients. "Pharmaceutically acceptable excipients" means diluents, auxiliary agents and/or vehicles used in pharmaceutics. A pharmaceutical composition alongside the compound expressed by the general formula 1 of this invention may include other active ingredients, including those having anticancer activity, provided, however, that they do not cause adverse effects.

The pharmaceutical composition according to this invention may be mixed with conventional pharmaceutical vehicles if necessary to be clinically used.

The vehicles used in pharmaceutical compositions according to this invention are vehicles used in pharmaceutics for the production of general forms, which includes the following: binders, lubricants, disintegrants, solvents, diluents, stabilisers, suspending agents, colorless agents, flavours are used in oral forms; antiseptic agents, solubilizers, stabilisers are used in injection forms; bases, diluents, lubricants, antiseptic agents are used in topical forms.

The object of this invention is also a method for producing a pharmaceutical composition.

The said object is achieved through the mixing of the active ingredient with an inert filler and/or solvent the distinctive feature of which is the fact that at least one compound expressed by the general formula 1 is used as an active ingredient.

Subject matter of this invention is also a medicinal product in tablets, capsules or injections comprising new active ingredient or new pharmaceutical composition intended to treat cancer.

More preferred medicinal products comprising new active ingredient or new pharmaceutical composition: the drugs intended to treat prostate cancer.

Subject matter of this invention is therapeutic cocktails for the treatment of cancer diseases (including prostate cancer) one of the components of which is the new medicinal product or new pharmaceutical composition comprising at least one compound expressed by the general formula 1 as an active ingredient.

A therapeutic cocktail for the treatment of prostate cancer may include other known drugs intended to treat cancer diseases alongside the medicinal product according to this invention.

In accordance to this invention the method for treatment of cancer diseases in humans and animals (including prostate cancer) consists in administration of the new medicinal product, new pharmaceutical composition or new therapeutic cocktail to a homeothermic animal or a human.

Medicinal products may be administered orally or parenterally (for example, intravenously, subcutaneously, abdominally or topically). Clinical dosage of the active ingredient expressed by the general formula 1 in patients may be adjusted depending on therapeutic efficacy and bioavailability of active ingredients in the organism, their metabolic rate and elimination rate, and depending on the patient's age, sex and disease stage, provided that daily dose for adults is usually 10~500 mg, preferably 50~300 mg. In view of this, when producing a medicinal product from a pharmaceutical composition in accordance with this invention in dosage units, it is necessary to take into account the abovementioned effective dosage, provided that each dosage unit of the drug shall contain 10~500 mg of the active ingredient expressed by the general formula 1, preferably 50~500 mg.

In accordance with instructions of a doctor or pharmacist, these drugs may be taken several times during particular periods of time (preferably from one to six times).

The following examples describe the synthesis of compounds expressed by the general formula 1 and assays thereof. Examples provided below are purely exemplary of this invention and not restrictive.

EXAMPLE 1

General method of producing 4-((R)-1-carboxy-1-methyl-2-methoxy-ethylamino)-2-fluoro-benzoic acid 2.1 and (R)-3-(4-carboxy-3-fluoro-phenylamino)-tetrahydrofuran-3-carboxylic acid 2.2. A mixture of (R)-stereoisomer of the amino acid 3.1 (85 mmole), 15.5 g (71 mmole) 4-bromo-2-fluorobenzoic acid 3.2, 39.3 g (284 mmole) $K_2CO_3$, 2.02 g (10.6 mmole) CuI and 2 g (14.3 mmole) 2-acetylcyclohexanone in 150 ml of dimethylformamide and 35 ml of water are mixed at 100° C. for two days. The reacting mass is vaporized in vacuum, the residue was treated with water and acidified with hydrochloric acid to pH 2-3 and vaporized in vacuum again. Was obtained 4-((R)-1-carboxy-1-methyl-2-methoxy-ethylamino)-2-fluoro-benzoic acid 2.1 (LC-MS (ESI) 272 $(M+H)^+$) and (R)-3-(4-carboxy-3-fluoro-phenylamino)-tetrahydro-furan-3-carboxylic acid 2.2 (LC-MS (ESI) 270 $(M+H)^+$), which is used in subsequent syntheses without further purification.

EXAMPLE 2

General method for preparation of methyl 4-((R)-1-methyl-2-methoxy-1-methoxycarbonyl-ethylamino)-2-fluoro-benzoate and 2.3 methyl (R)-3-(4-methoxycarbonyl-3-fluoro-phenylamino)-tetrahydrofuran-3-carboxylate 2.4. To the solution obtained in Example 1, 2.1 or 2.2 diacid in 150 ml of methanol, cooled in an ice bath, added 13 mL (177 mmol) of thionyl chloride. The resulting mixture was refluxed 15 hours, cooled to room temperature and concentrated in vacuo. To the residue was added 200 ml of ethyl acetate and a solution of 8.95 g (107 mmol) NaHCO3 in 100 ml water. Separate the organic layer was evaporated in vacuo and the residue chromatographed on silica gel, eluent-dichloromethane. To give methyl 4-((R)-1-methyl-2-methoxy-1-methoxycarbonyl-ethylamino)-2-fluoro-benzoate in a yield of 2.3 62% (LC-MS (ESI) 300 (M+H)+) or methyl (R)-3-(4-methoxycarbonyl-3-fluoro-phenylamino)-tetrahydrofuran-3-carboxylate with a yield of 2.4 58%: LC-MS (ESI) 298 $(M+H)^+$; $^1H$ NMR (CDCl$_3$, 400 MHz) δ 7.78 (t, J=8.8 Hz, 1H), 6.32 (dd, $J_1$=8.8 Hz, $J_2$=2.4 Hz, 1H), 6.21 (dd, $J_1$=13.6 Hz, $J_2$=2.4 Hz, 1H), 4.82 (brs, 1H), 4.18 (d, J=9.4 Hz, 1H), 4.07 (m, 2H), 4.00 (d, J=9.4 Hz, 1H), 3.88 (s, 3H), 3.77 (s, 3H), 2.71 (m, 1H), 2.29 (m, 1H).

EXAMPLE 3

General method for preparation of methyl 4-[(R)-3-(3-methyl-4-cyano-phenyl)-5-methyl-5-methoxymethyl-4-oxo-2-thioxo-imidazolidin-1-yl]-2-fluoro benzoate 1.1.1 or methyl 4-[(R)-3-(3-methyl-4-cyano-phenyl)-4-oxo-2-thioxo-7-oxa-1,3-diaza-spiro [4.4] non-1-yl]-2-fluoro-benzoate 1.1.2. A mixture of 41 mmol of methyl 4-((R)-1-methyl-2-methoxy-1-methoxycarbonyl-ethylamino)-2-fluoro-benzoate 2.3 or methyl (R)-3-(4-methoxycarbonyl-3-fluoro-phenylamino)-tetrahydrofuran-3-carboxylate, 2.4, 18.7 g (82 mmol) of 4-cyano-3-trifluoromethyl-benzolizotiotsianata 3.3, 2.9 ml of dimethyl sulfoxide and 16 ml of ethyl acetate was stirred at 85° C. 48 h, 2 mL of methanol was added and stirred for another 30 min at 85° C. The reaction mixture was cooled to 200 C, concentrated in vacuo and the residue chromatographed on silica gel, eluent-dichloromethane. Recrystallization from methanol gave 4-[(R)-3-(3-methyl-4-cyano-phenyl)-5-methyl-5-methoxymethyl-4-oxo-2-thioxoimidazolidin-1-yl]-2 1.1.1 fluoro-benzoate in a yield of 42% (LC-MS (ESI) 496 (M+H)+) or methyl 4-[(R)-3-(3-methyl-4-cyano-phenyl)-4 oxo-2-thioxo-7-oxa-1,3-diaza-spiro [4.4] non-1-yl]-2-fluoro-benzoate 1.1.2 yield 34%: LC-MS (ESI) 494 (M+H)$^+$; $^1$H NMR (CDCl$_3$, 400 MHz) δ 8.14 (t, J=8.0 Hz, 1H), 8.01 (d, J=8.4 Hz, 1H), 7.97 (d, J=2.9 Hz, 1H), 7.85 (dd, J$_1$=8.4 Hz, J$_2$=2.0 Hz, 1H), 7.27 (m, 2H), 4.42 (d, J=10.2 Hz, 1H), 4.15 (d, J=10.2 Hz, 1H), 3.99 (s, 3H), 3.96 (m, 1H), 3.76 (m, 1H), 2.73 (m, 1H), 2.47 (m, 1H).

EXAMPLE 4

General method for preparing 4-[(R)-3-(3-methyl-4-cyano-phenyl)-5-methyl-5-methoxymethyl-4-oxo-2-thioxo-imidazolidin-1-yl]-2-fluoro 1.2.1 benzoic acid or 4-[(R)-3-(3-methyl-4-cyano-phenyl)-4-oxo-2-thioxo-7-oxa-1,3-diaza-spiro [4.4] non-1-yl]-2-fluoro-benzoic acid 1.2.2. To a solution of 1.1.1 or 1.1.2 (0.41 mmol) in 3 ml of methanol pribavdyayut 16.5 mg (0.41 mmol) NaOH in 2 ml of water and the resulting mixture was stirred for 12 hours and then evaporated in vacuo. To the residue was added 10 ml of water and the resulting solution was acidified to pH 3 with hydrochloric acid. The precipitate was filtered off, washed with water and dried in vacuo. 1.1.1 acid obtained in a yield of 90%, LC-MS (ESI) 493 (M+H)+1.1.2 or acid to yield 92%, LC-MS (ESI) 490 (M+H)$^+$; $^1$H NMR (DMSO-d$_6$, 400 MHz) δ 13.53 (brs, 1H), 8.40 (d, J=8.4 Hz, 1H), 8.26 (s, 1H), 8.08 (dd, J$_1$=8.4 Hz, J$_2$=1.2 Hz, 1H), 8.03 (t, J=8.4 Hz, 1H), 7.57 (dd, J$_1$=11.2 Hz, J$_2$=1.2 Hz, 1H), 7.48 (dd, J$_1$=8.4 Hz, J$_2$=1.2 Hz, 1H), 4.43 (d, J=10.8 Hz, 1H), 3.94 (d, J=10.8 Hz, 1H), 3.75 (q, J=8.0 Hz, 1H), 3.53 (q, J=8.0 Hz, 1H), 2.58 (t, J=7.2 Hz, 2H).

EXAMPLE 5

General method for preparing 4-[(R)-3-(3-methyl-4-cyano-phenyl)-5-methyl-5-methoxymethyl-4-oxo-2-thioxo-imidazolidin-1-yl]-2-fluoro 1.3.1-benzamide or 4-[(R)-3-(3-methyl-4-cyano-phenyl)-4-oxo-2-thioxo-7-oxa-1,3-diaza-spiro [4.4] non-1-yl]-2-fluoro-benzamide 1.3.2. Acid A mixture of 0.37 mmol 1.2.1 or 1.2.2, 107 microns (0.55 mmol) N-(3-dimethylaminopropyl)-N'-ethylcarbodiimide hydrochloride (EDAC), 75 mg (0.55 mmol) of 1-hydroxybenzotriazole (HOBt), 26 mg of (0.48 mmol) ammonium chloride and 52 ml (0.37 mmol) of triethylamine in 3 ml of DMF was stirred 2 h. The reaction mixture was concentrated, the residue dissolved in dichloromethane, washed with 10% aqueous sodium carbonate, dried over sodium sulfate, concentrated and purified by HPLC. 1.3.1 amide Yield 51%, LC-MS (ESI) 491 (M+H)+. The yield amide 1.3.2 48%, LC-MS (ESI) 489 (M+H)$^+$; $^1$H NMR (DMSO-d$_6$, 400 MHz) δ 8.40 (d, J=8.0 Hz, 1H), 8.26 (d, J=1.6 Hz, 1H), 8.08 (dd, J$_1$=8.0 Hz, J$_2$=1.6 Hz, 1H), 7.92 (s, 1H), 7.79 (t, J=8.0 Hz, 1H), 7.76 (s, 1H), 7.53 (dd, J$_1$=10.8 Hz, J$_2$=1.6 Hz, 1H), 7.43 (dd, J$_1$=8.0 Hz, J$_2$=1.6 Hz, 1H), 4.42 (d, J=10.6 Hz, 1H), 3.94 (d, J=10.6 Hz, 1H), 3.75 (m, 1H), 3.53 (m, 1H), 2.58 (m, 2H).

EXAMPLE 6

General method for preparation of methyl 4-[(R)-3-(3-methyl-4-cyano-phenyl)-5-methyl-5-methoxymethyl-4-oxo-2-thioxo-imidazolidin-1-yl]-2-1.1.1 fluoro-benzoate, methyl 4-[(R)-3-(3-methyl-4-cyano-phenyl)-4-oxo-2-thioxo-7-oxa-1,3-diaza-spiro [4.4] non-1-yl]-2-fluoro-1.1.2 benzoate, isopropyl 4-[(R)-3-(3-methyl-4-cyano-phenyl)-4-oxo-2-thioxo-7-oxa 1,3-diaza-spiro [4.4] non-1-yl]-2-fluoro-benzoate 1.1.3 or cyclopropyl 4-[(R)-3-(3-methyl-4-cyano-phenyl)-4 oxo-2-thioxo-7-oxa-1,3-diaza-spiro [4.4]-2-fluoro-benzoate 1.1.4 non-1-yl]. Acid To a solution of 1.2.1 or 1.2.2, 150 ml of the appropriate alcohol, cooled in an ice bath, was added 13 (177 Ml mmol) of thionyl chloride. The resulting mixture was refluxed 15 hours, cooled and evaporated to 200 C. To the residue was added 200 ml of ethyl acetate and a solution of 8.95 g (107 mmol) NaHCO3 in 100 ml of water. Separate the organic layer was evaporated in vacuo and the residue chromatographed on silica gel, eluent-dichloromethane. 1.1.1 esters obtained (LC-MS (ESI): 496 (M+H)+), 1.1.2 (LC-MS (ESI): 494 (M+H)+), 1.1.3 (LC-MS (ESI) 522 (M+H)+) or 1.1.4 (LC-MS (ESI): 500 (M+H)+) to yield 55-62%.

EXAMPLE 7

Determination of antagonistic activity of the new compounds of general formula 1 and their analogues with respect to androgen receptors. The ability of the new compounds of general formula 1 and their analogues block androgen receptors is determined by their effectiveness ingbirovaniya sitmulirovannoy dihydrotestosterone expression of prostate-specific antigen (PSA) in the human prostate cancerous cells, LNCap, bank obtained from the American Tissue Culture (ATCC, USA). These cells are sensitive to 5-α-dihydrotestosterone (DHT) and produce cancerous marker (PSA) in its presence. Cells were grown in RPMI 1640 medium (Invitrogen, USA) containing 10% calf serum (Hyclone, USA), 1% antibiotic/antifungal mixture (Sigma, USA) and 4.5% glucose. Before experiments, the cells were washed and suspended in the same medium, where, however, calf serum was replaced with serum-treated to remove traces of charcoal hormones. Cells were dispensed at 100 1 (10 000 cells) in cell 96 lunochnoyh dies and left for 4 days in an incubator at 370° S (100% humidity) in an atmosphere of 95% air/5% CO2. After 4 day incubation, the cells were added successively the compound of formula 1 or their analogues in different concentrations and 20 nM DHT (concentration corresponding to 80-90% of the maximum stimulation). Cells were allowed to stand for further 5 days under the same incubation conditions. Then nadkletochnoy environmental samples were taken for analysis on the content of the PSA. The analysis was performed according to the protocol recommended by the kit manufacturer to determine the PSA (Alpha Diagnostic International, USA). After wetting holes on the bottom affixed containing antibodies against PSA, they added 25 ul of samples and then 100 L of antibodies as anti-PSA, which konyugtrovana horseradish peroxidase. After a 30 minute incubation at room temperature, the wells were removed, the wells were washed several times and poured into the wells, 100 ul of a chromogenic peroxidase substrate. Plates were incubated for 15 minutes at room temperature, the wells were added 50 mcl of stop solution and the intensity of color which developed was measured by absorbance at 450 nm. The intensity of the absorption is proportional to the concentration of PSA in the sample. Determination of the concentration dependences blokiovaniya androgen receptor possible to determine IC50 and Ki, which are presented in Table. 1.

TABLE 1

| | | IC$_{50}$, nM | K$_i$, nM | |
|---|---|---|---|---|
| I | [structure] | 124.7 | 28.6 | MDV3100 |
| II | [structure] | 145.3 | 34.9 | H030-0016B |
| III | [structure] | 171.9 | 33.3 | ARN-509 |
| IV | [structure] | 83.5 | 20.1 | ONC1-0013B |
| 1.1.2 | [structure] | 33.0 | 5.6 | |
| 1.2.2 | [structure] | | | |
| 1.3.2 | [structure] | 79.6 | 15.4 | |

As it is seen from Table. 1, the new compounds are more active than the known analogues, with the most active of these is the compound 1.1.2 with Ki=5.6 nM, which is 5.1 times more active MDV3100, 5.9 times more active ARN-509, and 3.6 times more active ONC1-0013B. Note that the higher activity of the preparations can be used in cancer treatment, lower doses, resulting in a reduction of side effects and toxicity.

EXAMPLE 8

Preparation of the drug in tablet form. Mix 1600 mg of starch, 1600 mg of milled lactose, the talc, and 400 mg of 1000 mg of compound 1.1.2. The resulting pharmaceutical composition is pressed in the bar. Bar was comminuted into granules and sifted through sieve to collect granules of 14-16 mesh. The obtained granules were tableted by a suitable form tablets each weighing 560 mg.

EXAMPLE 9

Preparation of medicament in form of capsules. 1.1.2 intimately mixed compounds with lactose powder in ratio 2:1. The resulting pharmaceutical composition is packaged in 300 mg gelatin capsules of suitable size.

EXAMPLE 10

Preparation of medicament in form of compositions for intramuscular, intraperitoneal or subcutaneous injection. 500 mg of the compound admixed 1.1.2 with 300 mg of chlorobutanol, 2 ml of propylene glycol and 100 mL of injectable water. The resulting solution was filtered and placed into 1 ml ampoules which are sealed.

INDUSTRIAL APPLICABILITY

The invention can be used in human and veterinary medicine.

What is claimed:
1. A composition, comprising:
a compound that is an (R)-stereoisomer of a substituted 2-thioxo-imidazolidine-4-one having a structure according to general formula 1,

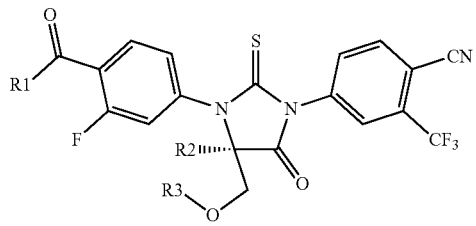

wherein:
R1 is OH, NH$_2$, or a OR4 group;
R2 and R3 are methyl, or R2 and R3 in combination form a CH2—CH2 group; and
R4 is C$_1$-C$_4$ alkyl or cyclopropyl.
2. The composition of claim 1, wherein the compound has a structure according to general formula 1.1 or 1.2,

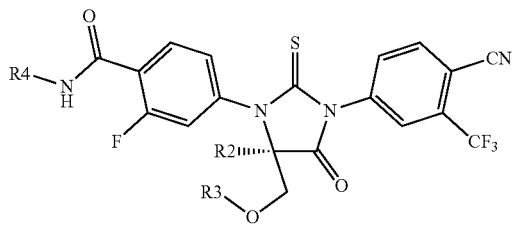

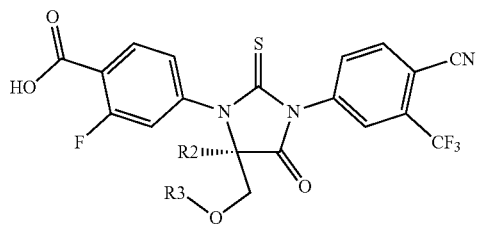

wherein R2, R3, and R4 are as defined previously.
3. The composition of claim 1, wherein the compound is methyl 4-[(R)-3-(3-methyl-4-cyano-phenyl)-5-methyl-5-methoxymethyl-4-oxo-2-thioxo-imidazolidine-1-yl]-2-fluoro-benzoate according to formula 1.1.1,

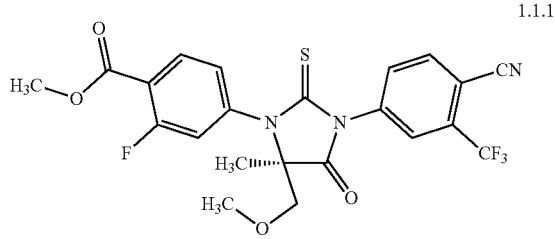 [SMILES: COC[C@]1(C)C(=O)N(c2ccc(C#N)c(C(F)(F)F)c2)C(=S)N1c1ccc(C(=O)OC)c(F)c1]

methyl 4-[(R)-3-(3-methyl-4-cyano-phenyl)-4-oxo-2-thioxo-7-oxa-1,3-diaza-spiro[4.4]non-1-yl]-2-fluoro-benzoate according to formula 1.1.2,

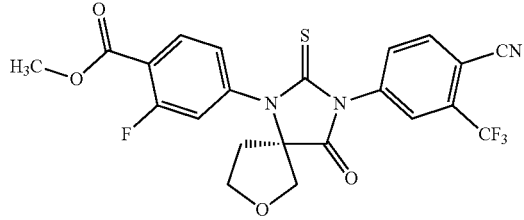

isopropyl 4-[(R)-3-(3-methyl-4-cyano-phenyl)-4-oxo-2-thioxo-7-oxa-1,3-diaza-spiro[4.4]non-1-yl]-2-fluoro-benzoate according to formula 1.1.3,

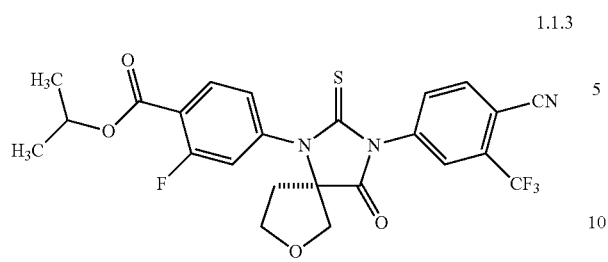

cyclopropyl 4-[(R)-3-(3-methyl-4-cyano-phenyl)-4-oxo-2-thioxo-7-oxa-1,3-diaza-spiro[4.4]non-1-yl1-2-fluoro-benzoate according to formula 1.1.4,

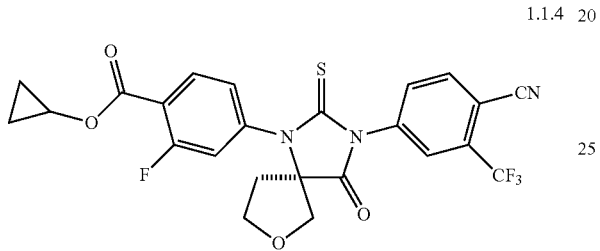

4-[(R)-3-(3-methyl-4-cyano-phenyl)-5-methyl-5-methoxymethyl-4-oxo-2-thioxo-imidazolidine-1-yl]-2-fluoro-benzoic acid according to formula 1.2.1,

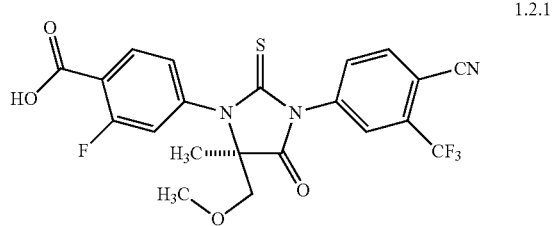 [SMILES: COC[C@]1(C)C(=O)N(c2ccc(C#N)c(C(F)(F)F)c2)C(=S)N1c1ccc(C(=O)O)c(F)c1]

4-[(R)-3-(3-methyl-4-cyano-phenyl)-4-oxo-2-thioxo-7-oxa-1,3-diaza-spiro[4.4]non-1-yl]-2-fluoro-benzoic acid according to formula 1.2.2,

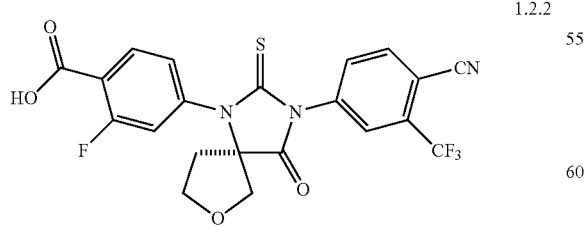

4-[(R)-3-(3-methyl-4-cyano-phenyl)-5-methyl-5-methoxymetyl-4-oxo-2-thioxo-imidazolidine-1-yl]-2-fluoro-benzamide according to formula 1.3.1,

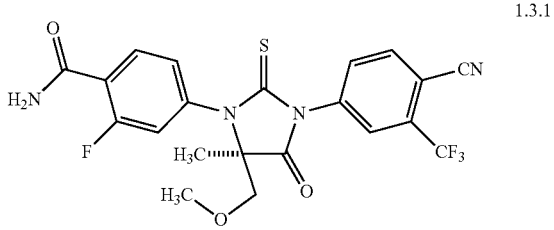 [SMILES: COC[C@]1(C)C(=O)N(c2ccc(C#N)c(C(F)(F)F)c2)C(=S)N1c1ccc(C(N)=O)c(F)c1]

or
4-[(R)-3-(3-methyl-4- cyano-phenyl)-4-oxo-2-thioxo-7-oxa-1,3-diaza-spiro[4.4]non-1-yl]-2- fluoro-benzamide according to formula 1.3.2,

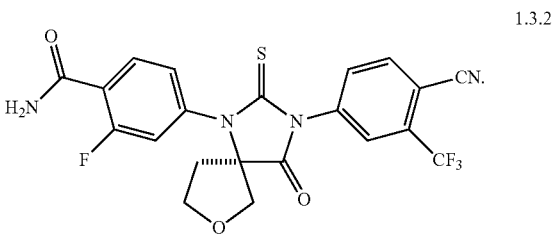 [SMILES: N#Cc1ccc(N2C(=O)[C@]3(CCOC3)N(c3ccc(C(N)=O)c(F)c3)C2=S)cc1C(F)(F)F]

4. The composition of claim 1, wherein the compound is 4-((R)-1-carboxy-1-methyl-2-methoxy-ethylamino)-2-fluoro-benzoic acid according to formula 2.1,

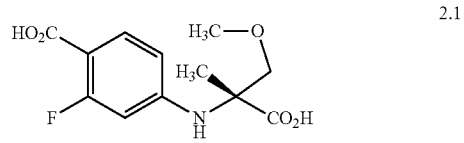 [SMILES: COC[C@@](C)(Nc1ccc(C(=O)O)c(F)c1)C(=O)O]

(R)-3-(4-carboxy-3-fluoro-phenylamino)-tetrahydro-furan-3-carboxylic acid according to formula 2.2,

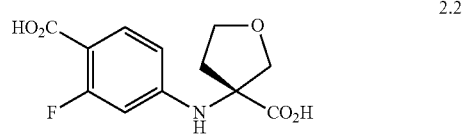 [SMILES: O=C(O)c1ccc(N[C@]2(C(=O)O)CCOC2)cc1F]

methyl 4-((R)-1-methyl-2-methoxy-1-methoxycarbonyl-ethylamino)-2-fluoro-benzoate according to formula 2.3,

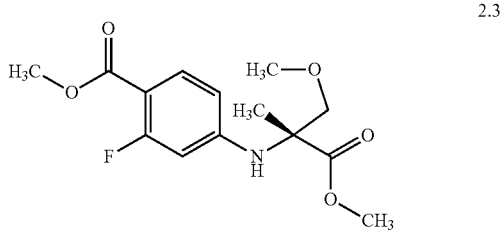

or methyl (R)-3-(4-methoxycarbonyl-3-fluoro-phenylamino)-tetrahydrofuran-3-carboxylate according to formula 2.4

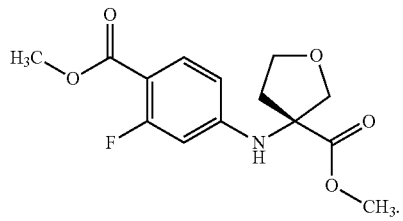

2.4

5. A medicament for the treatment of cancer, comprising: a compound that is an (R)-stereoisomer of a substituted 2-thioxo-imidazolidine-4-one having a structure according to general formula 1,

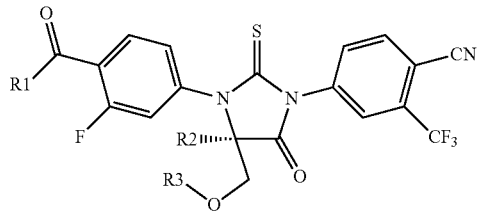

1 wherein:
R1 is OH, NH$_2$, or a OR4 group;
R2 and R3 are methyl, or R2 and R3 in combination form a CH$_2$—CH$_2$ group; and
R4 is C$_1$-C$_4$ alkyl or cyclopropyl;
and wherein the compound acts as an androgen receptor antagonist.

6. A pharmaceutical composition for treatment of cancer, the pharmaceutical composition having properties of an androgen receptor antagonist, comprising a therapeutically effective amount of a compound that is an (R)-stereoisomer of a substituted 2-thioxo-imidazolidine-4-one having a structure according to general formula 1,

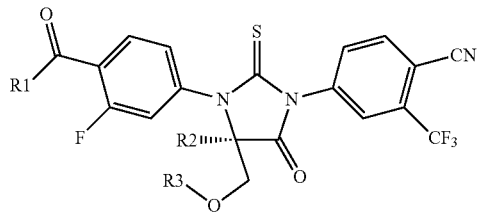

1 wherein:
R1 is OH, NH$_2$, or a OR4 group;
R2 and R3 are methyl, or R2 and R3 in combination form a CH$_2$—CH$_2$ group; and
R4 is C$_1$-C$_4$ alkyl or cyclopropyl.

7. The pharmaceutical composition of claim 6, further comprising one or more pharmaceutically acceptable excipients.

8. The pharmaceutical composition of claim 6, further comprising an inert filler or solvent.

9. The pharmaceutical composition of claim 6, that is in the form of tablets, capsules, or injections.

10. The pharmaceutical composition of claim 6, wherein the parmaceutical composition is formulated for treatment of a prostate cancer.

11. The pharmaceutical composition of claim 6, wherein the pharmaceutical composition is formulated for treatment of a breast cancer.

12. A method for preparing compounds according to formulas 2.1 and 2.2 of claim 4, comprising reacting an (R)-stereoisomer of an amino acid according to formula 3.1 with 4-bromo-2-fluorobenzoic acid according to formula 3.2 in dimethylformamide in the presence of CuI and a base,

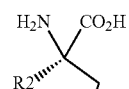

3.1

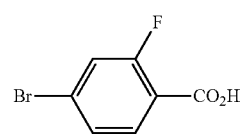

3.2 wherein R2=R3=CH$_3$ or R2 in combination with R3 form a CH$_2$—CH$_2$ group.

13. A method for preparing compounds according to formulas 2.3 and 2.4 of claim 4, comprising reacting an (R)-stereoisomer of an appropriate diacid according to formula 2.1 and 2.2 with alcohol in the presence of thionyl chloride,

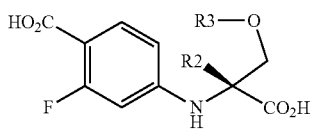

2.1, 2.2 wherein R2=R3=CH$_3$ or R2 in combination with R3 form a CH$_2$—CH$_2$ group.

14. A method for producing compounds according to formulas 1.1.1 and 1.1.2 of claim 3, comprising reacting an (R)-stereoisomer of an appropriate diester according to formula 2.3 and 2.4 with 4-cyano-3-trifluoromethyl-benzyl isothiocyanate according to formula 3.3 at an elevated temperature,

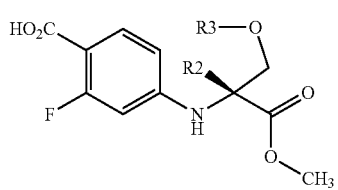

2.3, 2.4

-continued

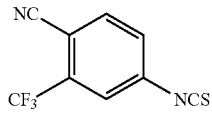

3.3 wherein R2 and R3 are as defined previously.

15. A method for producing compounds according to the formula 1.2.1 and 1.2.2 of claim 3, comprising performing alkaline hydrolysis of the (R)-stereoisomers of the esters of formula 1.1.1 and 1.1.2, respectively.

16. A method for producing esters according to formula 1.1 of claim 2, comprising reacting an acid according to formula 1.2 with alcohol and thionyl chloride.

17. A method for producing amides according to formulas 1.3.1 and 1.3.2, comprising reacting an acid of the formula 1.2 of claim 2 with ammonium chloride in the presence of N-(3-dimethylaminopropyl)-N'-ethylcarbodiimide, 1-hydroxybenzotriazole and triethylamine in dimethylformamide.

18. A method of producing the pharmaceutical composition of claim 6, comprising mixing a compound according to formula 1 with one or more inert fillers and/or solvents.

19. A method of treating a cancer disease that is mediated by an activity of androgen receptors, which comprises administering a compound according to formula 1 of claim 2.

* * * * *